US010557808B2

(12) United States Patent
Furukawa

(10) Patent No.: US 10,557,808 B2
(45) Date of Patent: Feb. 11, 2020

(54) METHOD AND APPARATUS FOR DISCRIMINATING RESIN

(71) Applicant: Shimadzu Corporation, Kyoto (JP)

(72) Inventor: Hiroaki Furukawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 146 days.

(21) Appl. No.: 15/877,942

(22) Filed: Jan. 23, 2018

(65) Prior Publication Data

US 2019/0227009 A1   Jul. 25, 2019

(51) Int. Cl.
  *G01N 23/02* (2006.01)
  *G01N 23/2206* (2018.01)
  *G01N 23/223* (2006.01)
(52) U.S. Cl.
  CPC ....... *G01N 23/2206* (2013.01); *G01N 23/223* (2013.01); *G01N 2223/05* (2013.01); *G01N 2223/076* (2013.01); *G01N 2223/60* (2013.01)
(58) Field of Classification Search
  CPC .............. G01N 23/22; G01N 23/2204; G01N 23/2209; G01N 23/223; G01N 2223/076; G01N 2223/1016; G03F 7/2039
  See application file for complete search history.

(56) References Cited

U.S. PATENT DOCUMENTS

2013/0208850 A1*  8/2013  Schmitt ................. G01N 23/20
                                                                  378/4

FOREIGN PATENT DOCUMENTS

| JP | H06-337252 | 12/1994 |
| JP | 2006-162468 | 6/2006 |
| JP | 2010-223908 A | 10/2010 |

OTHER PUBLICATIONS

Japanese Office Action dated Aug. 21, 2018, in connection with corresponding JP Application No. 2015-139462 (7 pgs., including English translation).

* cited by examiner

*Primary Examiner* — David P Porta
*Assistant Examiner* — Mamadou Faye
(74) *Attorney, Agent, or Firm* — Maier & Maier, PLLC

(57) ABSTRACT

A resin discriminating apparatus includes an X-ray tube which emits X-rays, an X-ray detector which detects X-rays emitted from a sample irradiated with X-rays, a data processing section which creates a spectrum on the basis of a detection signal obtained by the X-ray detector, a peak extraction section which extracts a spectral line due to Compton scattering and a spectral line due to Rayleigh scattering derived from a target element of the X-ray tube on the spectrum, and obtains a peak intensity, and a discrimination section which calculates a scattering intensity ratio which is a ratio of the Rayleigh scattering intensity to the Compton scattering intensity and discriminates the type of resin contained in the sample from the scattering intensity ratio.

6 Claims, 3 Drawing Sheets

METHOD AND APPARATUS FOR DISCRIMINATING RESIN

FIELD

The invention relates to a resin discriminating apparatus and a resin discriminating method for discriminating the type of resin, and more particularly, to a resin discriminating apparatus and a resin discriminating method for irradiating a sample with excited X-rays and discriminating the type of resin, using X-rays emitted from the sample, accordingly.

BACKGROUND

As a quantitative method using fluorescent X-ray analysis, a calibration curve method and a fundamental parameter method (hereinafter referred to as "FP method") are well known. In the calibration curve method, a calibration curve representing a relation between the X-ray intensity and the element content (or concentration) is prepared in advance from the result obtained by measuring the standard sample, and using the calibration curve, the element content is obtained from the X-ray intensity value obtained by measurement on the target sample. On the other hand, in the FP method, the element content is obtained by theoretical intensity calculation from the X-ray intensity value obtained by measuring a target sample. Although the FP method is inferior to the calibration curve method in terms of quantitative accuracy, there is an advantage that quantification can be performed simply without requiring a standard sample.

A method described in Patent Literature 1, for example, is known as a method for performing quantitative determination on a sample containing an element that cannot measure fluorescent X-rays, such as hydrogen and carbon, for example, an organic compound such as a resin, by the FP method. In this method, assuming the main component elements of the resin contained in the sample, fluorescent X-rays are used for each component other than the main component, while scattered X-rays are used for the main component, the actually measured intensity and the theoretical intensity for the sample are compared and the quantitative values of the main component and other various components are determined by the FP method. In such a quantitative method, it is possible to estimate the quantitative value of various components, but since it is assumed for the main component element, it is difficult to specify the organic compound, and for example, it is not possible to discriminate the type of resin contained in the sample. Therefore, the quantitative value obtained by the above method can only be used as information for pretreatment to classify a resin from other substances (for example, metals), and in order to specify the type of resin, there is an actual situation in which further process is performed.

[Patent Literature 1] JP-A-2010-223908

SUMMARY

The invention has been made to solve the aforementioned problems, and a main object thereof is to provide a resin discriminating apparatus and a resin discriminating method capable of discriminating the type of resin contained in the sample from X-rays emitted from the sample when the sample is irradiated with X-rays.

In order to solve the aforementioned problem, a resin discriminating apparatus according to the invention includes:

a) an X-ray source which emits X-rays;
b) an X-ray detector which detects X-rays emitted from a sample irradiated with X-rays from the X-ray source;
c) a spectrum creating unit which creates a spectrum on the basis of a detection signal obtained by the X-ray detector;
d) a scattering intensity ratio calculation unit which detects a spectral line due to Compton scattering and a spectral line due to Rayleigh scattering derived from a target element of the X-ray source on the spectrum, and calculates a scattering intensity ratio which is a ratio of the Compton scattering intensity and the Rayleigh scattering intensity; and
e) a resin type discrimination unit which discriminates the type of resin contained in the sample from the scattering intensity ratio.

The invention has been made by finding the fact that Rayleigh scattered X-rays and Compton scattered X-rays mainly derived from the target element of the X-ray source appears on a spectrum obtained from X-rays emitted from the sample when the sample containing the resin is irradiated with X-rays from the X-ray source, and the ratio of the Rayleigh scattering intensity to the Compton scattering intensity varies depending on the type of resin contained in the sample. Here, the resin is not limited to a solid resin such as plastics, but includes resins in various forms such as a liquid state and a powder state. The resin also includes natural resins as well as synthetic resins.

According to the invention, the resin discriminating apparatus further includes a storage section which stores a scattering intensity ratio previously obtained for a plurality of known resins, and the resin type discrimination unit may discriminate the type of resin contained in the sample, by comparing the scattering intensity ratio calculated by the scattering intensity ratio calculation unit with the plurality of scattering intensity ratios stored in the storage section.

In this case, the scattering intensity ratio of the known resin stored in the storage section may be a value obtained from the theoretical intensity of Compton scattering and Rayleigh scattering calculated from the contained element or structure of the resin, and may be a value obtained from intensity (actually measured intensity) of the Compton scattering and Rayleigh scattering actually measured for known resins. In such a configuration, the resin type discrimination unit discriminates the resin of the scattering intensity ratio having the smallest difference from the scattering intensity ratio calculated by the scattering intensity ratio calculation unit, for example, among the scattering intensity ratios stored in the storage section, as the type of resin contained in the sample.

Further, the resin type discrimination unit may obtain a relational expression in which a plurality of scattering intensity ratios stored in the storage section is set as independent variables and a scattering intensity ratio calculated for the sample is set as a dependent variable by regression analysis, and may discriminate the type of the resin contained in the sample from the coefficients of the respective independent variables in the obtained relational expression. In this case, it is possible to estimate that the coefficients of each independent variable are the mixing ratio of the resin contained in the sample. Further, all of the coefficients of each independent variable in the obtained relational expression may be estimated as the mixing ratio of the resin, but only the variable larger than the predetermined set minimum value may be estimated as a mixing ratio of the resin. Specifically, for example, when the value of the coefficient is larger than the set minimum value, it is discriminated that the known resin corresponding to the independent variable (the scattering intensity ratio stored in the storage section) having the coefficient is included in the sample at the ratio of the coefficient. If it is determined that the value of the coefficient is equal to or less than the set minimum value, it is discriminated that the known resin corresponding to the independent variable having the coefficient is not included in the sample. According to such a configuration, the resin corresponding to the term caused by the detection error of the X-ray detector among the terms of the independent variables of the obtained relational expression can be prevented from being erroneously determined as one of the types of the resin contained in the sample.

Depending on the types of resin, some resins contain elements emitting fluorescent X-rays such as chlorine (Cl) and sulfur (S). When such resin is irradiated with X-rays, the fluorescent X-ray spectrum derived from these elements is obtained. Therefore, when such a resin is used as a sample, the resin type discrimination unit may detect fluorescent X-rays emitted from the sample on the spectrum, and may discriminate the type of resin contained in the sample, from the intensity of the fluorescent X-rays and the scattering intensity ratio calculated by the scattering intensity ratio calculation unit.

In the aforementioned resin discriminating apparatus of the invention, it is preferable to include a discrimination result display section which displays a result discriminated by the resin type discrimination unit. In particular, in the case of the aforementioned configuration in which the type of resin is discriminated by the regression analysis, the solution (relational expression) is not always one. Therefore, when a plurality of solutions (relational expressions) is obtained and a plurality of different determination results is obtained, the determination results are printed or displayed on the display screen, and the resin contained in the sample may be determined from the results selected by the analyzer among the determination results. Further, when a plurality of relational expressions is obtained, the type of resin contained in the sample is discriminated from coefficients of each independent variable in the relational expression for each relational expression, and the degree of coincidence between the scattering intensity ratio obtained from the relational expression and the scattering intensity ratio calculated by the scattering intensity ratio calculation unit may be obtained. Further, when the type of resin and the degree of coincidence included in the sample discriminated by the resin discrimination unit for each of the plurality of relational expressions are printed or displayed on the display screen, the analyzer can discriminate the type of resin contained in the sample with reference to the degree of coincidence.

Another aspect of the invention is a resin discriminating method corresponding to the resin discriminating apparatus described above, the method including: irradiating a sample with X-rays emitted from an X-ray source; analyzing X-rays emitted from the sample accordingly; calculating a scattering intensity ratio which is a ratio of a Compton scattering intensity to a Rayleigh scattering intensity derived from a target element of the X-ray source; and discriminating the type of resin contained in the sample from the scattering intensity ratio.

In the above resin discriminating method, the type of resin contained in the sample may be discriminated by comparing the scattering intensity ratio calculated for the sample with a scattering intensity ratio obtained in advance for a plurality of known resins, a relational expression in which a scattering intensity ratio determined in advance for a plurality of known resins is set as an independent variable and a scattering intensity ratio calculated for the sample is set as a dependent variable may be obtained by regression analysis, and a type and a mixing ratio of the resin contained in the sample may be discriminated from the coefficients of each independent variable in the obtained relational expression.

Further, X-rays emitted from the sample may be analyzed in accordance with irradiation of X-rays on the sample to calculate the intensity of fluorescent X-rays emitted from the sample, and the type of resin that emits fluorescent X-rays, such as chlorine (Cl) or sulfur (S), other than the resin contained in the sample may be discriminated from the intensity of the fluorescent X-rays and the scattering intensity ratio calculated for the sample.

As described above, according to the resin discriminating apparatus and the resin discriminating method of the invention, by analyzing X-rays emitted from the sample when the sample is irradiated with X-rays, it is possible to discriminate the type of resin contained in the sample.

DETAILED DESCRIPTION OF THE FIGURE

DESCRIPTION OF EMBODIMENTS

Figure 1:
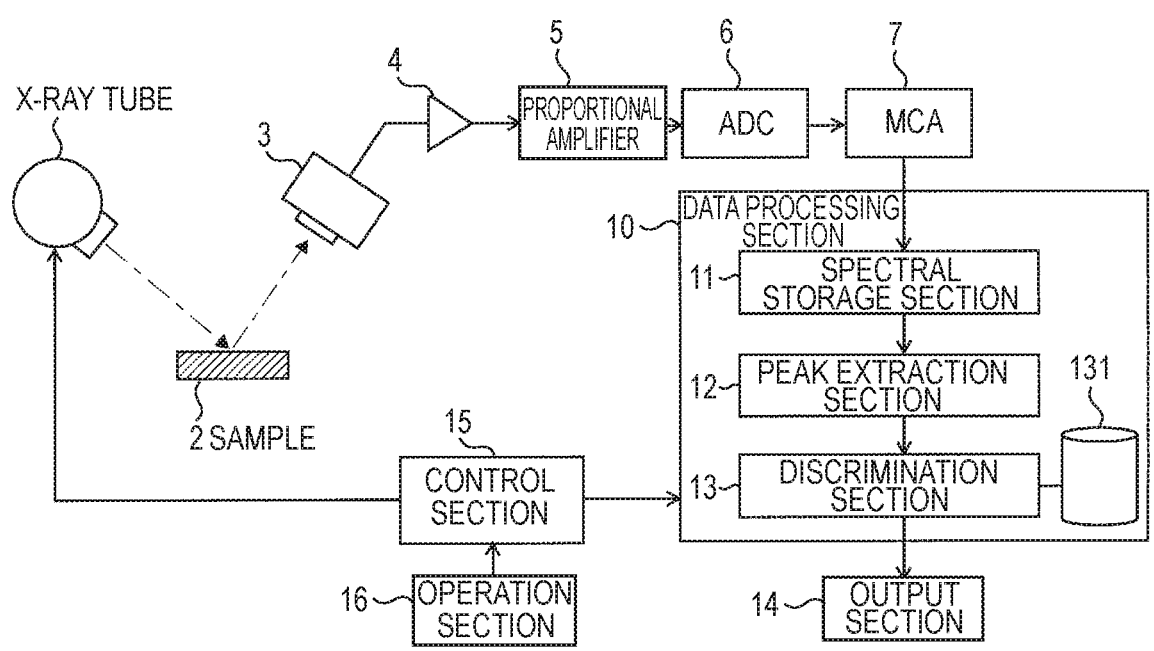
FIG. 1 is a schematic configuration diagram of an example of a fluorescent X-ray analyzer illustrating an embodiment of a resin discriminating apparatus according to the invention.

First, a fluorescent X-ray analyzer which is an example of a resin discriminating apparatus according to the invention will be described. FIG. 1 is a schematic configuration diagram of an energy dispersive fluorescent X-ray analyzer.

In FIG. 1, under the control of a control section 15, when the excited X-rays emitted from an X-ray tube 1 with a target material as rhodium (Rh) hit a sample 2, the fluorescent X-rays excited by the excited X-rays are emitted from the sample 2, are incident on an X-ray detector 3 such as a silicon drift detector, and are detected as a current signal. Some parts of the excited X-rays hitting the sample 2 are scattered by the sample 2, and such scattered X-rays are also detected by the X-ray detector 3. The detected current is integrated inside the X-ray detector 3, and its integration is reset when exceeding a certain time. As a result, the output signal of the X-ray detector 3 becomes a stepped current pulse signal. The height of each stage of this signal corresponds to the energy of each element contained in the sample 2. This current pulse signal is input to a preamplifier 4 and further to a proportional amplifier 5 including a waveform shaping circuit, and the current pulse signal is formed into a pulse of a suitable shape having a wave height corresponding to the height of each stage and is output.

The A/D converter (ADC) 6 digitizes the analog signal of the pulse wave shape at a predetermined sampling period. A multi-channel analyzer (MCA) 7 discriminates each pulse in accordance with the peak value of the digitized pulse signal, then counts each of the pulses, and creates a wave height distribution diagram, that is, an X-ray spectrum, and inputs the X-ray spectrum to a data processing section 10. The data constituting the X-ray spectrum is stored in a spectrum storage section 11. As it will be described later, in the X-ray spectrum, spectral lines unique to each element appear as peaks at positions corresponding to the energy values of fluorescent X-rays emitted from elements contained in the sample to be analyzed. Further, peaks of spectral lines of Compton scattered X-rays and Rayleigh scattered X-rays derived from target elements of the X-ray tube 1 also appear. In the data processing section 10, a peak extraction section 12 detects each peak appearing on the X-ray spectrum and extracts peaks of a target element or compound. A discrimination section 13 performs discriminating process of the type of resin contained in the sample, using the intensity of each extracted peak, that is, the X-ray intensity value. In this embodiment, a characteristic resin discriminating process is executed in this discrimination section 13.

Figure 2:
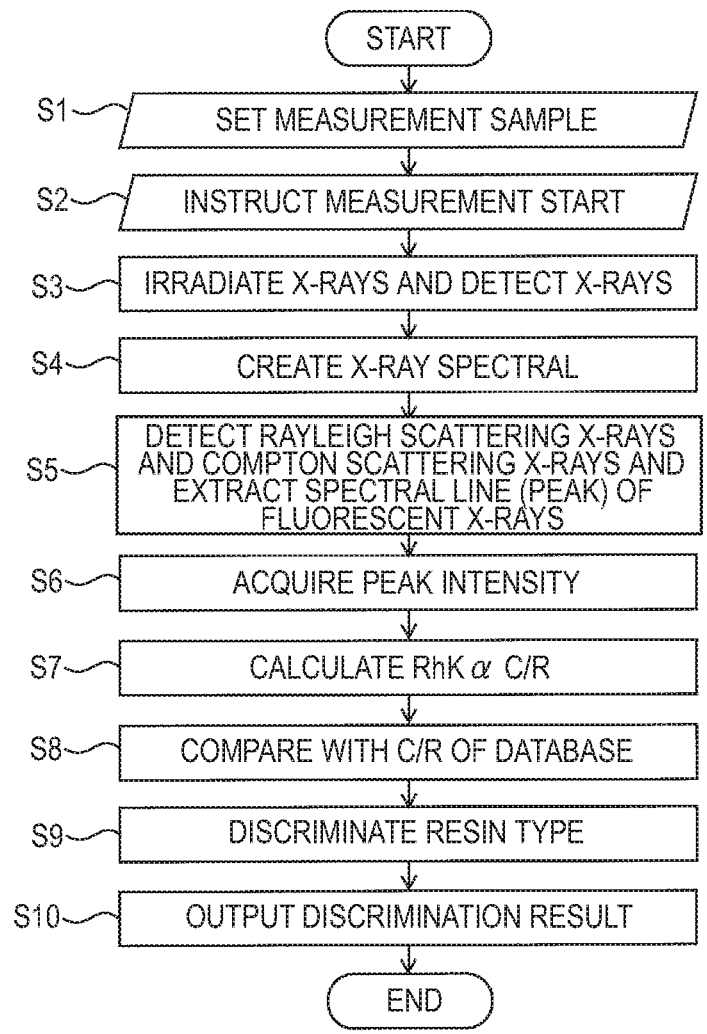
FIG. 2 is a flowchart of resin discrimination process in the embodiment.

Next, the procedure of resin discriminating process according to this embodiment will be described with reference to the flowchart of FIG. 2.

When the sample 2 is set at a predetermined position (step S1) and the start of measurement is instructed by an operation section 16 (step S2), the sample 2 is irradiated with X-rays and X-rays emitted from the sample 2 are detected by the X-ray detector 3 (step S3). Subsequently, the data processing section 10 creates an X-ray spectrum on the basis of the detection signal of the X-ray detector 3 (step S4), and the peak extraction section 12 extracts the peak due to the Compton scattered rays of the RhKα ray on the X-ray spectrum, the peak due to the Rayleigh scattered rays of the RhKα ray, and the peak of the fluorescent X-ray spectrum, and obtains the intensities thereof (steps S5 and S6). Further, the peak extraction section 12 also obtains the peak energy together with the peak intensity of the fluorescent X-ray spectrum.

The discrimination section 13 calculates the ratio (corresponding to the scattering intensity ratio of the invention, hereinafter referred to as a "C/R ratio") between the peak intensity due to the Compton scattered rays of the RhKα rays and the peak intensity due to the Rayleigh scattered rays of the RhKα rays (step S7). Further, the calculated C/R ratio is compared with the C/R ratio of the database stored in a storage section 131 in advance (step S8) to discriminate the type of resin contained in the sample 2 (step S9).

Figure 3:
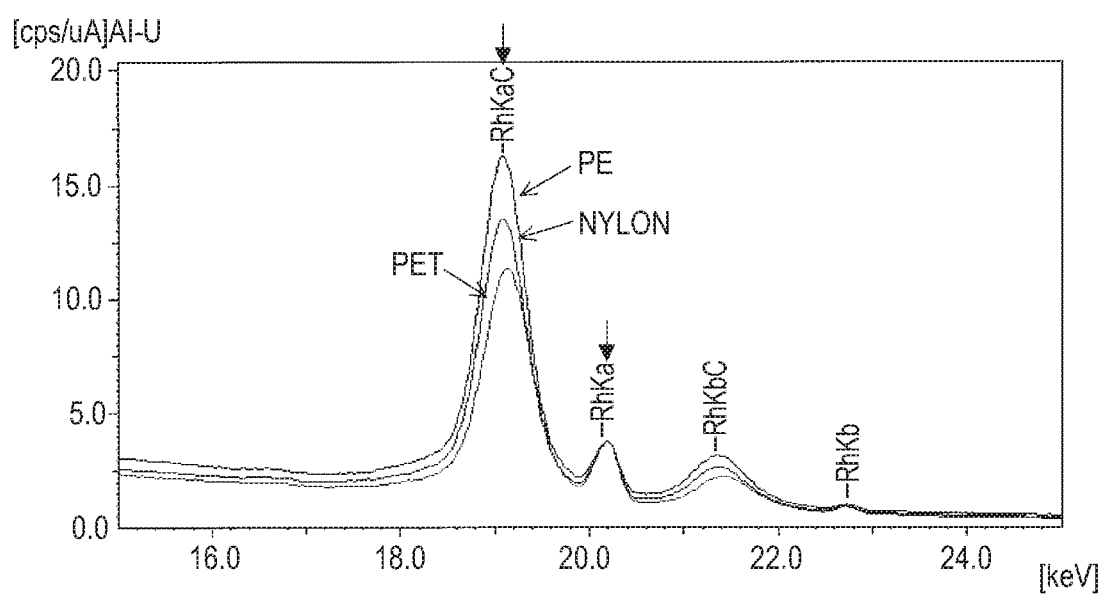
FIG. 3 is a diagram illustrating the results obtained by measuring fluorescent X-ray spectra of three types of pure resin materials.

Here, it is assumed that a table as illustrated in the following Table 1 is stored in the storage section 131. As the C/R ratio of the known resin type illustrated in Table 1, the C/R ratio obtained in advance using the apparatus according to this example may be used for a sample (resin pure substance) made of only various resins, or the C/R ratio may be obtained from the theoretical values of Compton scattering intensity and Rayleigh scattering intensity calculated from the composition of various resins. FIG. 3 illustrates examples of fluorescent X-ray spectra of three types of resin pure substances (polyethylene (PE), nylon, polyethylene terephthalate (PET)). In FIG. 3, the fourth peak from the right with the arrow and the third peak from the right indicate Compton scattered rays and Rayleigh scattered rays of RhKα ray, respectively. The C/R ratio can be obtained from the peak intensity of Compton scattered rays and the peak intensity of Rayleigh scattered rays of each resin.

TABLE 1

| | Resin type | | | | | | |
|---|---|---|---|---|---|---|---|
| | PE | PP | ABS | Nylon | PC | Acrylic | PET | ... |
| C/R ratio | 6.83 | 6.68 | 5.64 | 5.01 | 4.61 | 4.40 | 3.85 | ... |

For example, the discrimination section 13 obtains the difference between the C/R ratio calculated in step S7 and each C/R ratio in the table, extracts the resin type with the C/R ratio having the smallest difference, and determines the resin type as the type of resin contained in the sample. Also, it is determined whether or not the value of the calculated C/R ratio is included in a predetermined numerical range centered on the C/R ratio value illustrated in Table 1 (for example, a range of ±0.1), and when the value is included in the numerical range, the resin type is determined as the type of resin contained in the sample.

Further, when the peak of the fluorescent X-ray spectrum is extracted, the type of resin contained in the sample may be determined from the peak information (peak energy and peak intensity) and the aforementioned C/R ratio. Since the peak information of the fluorescent X-ray spectrum indicates that elements such as chlorine (Cl) or sulfur (S) are contained in the resin, it is possible to more accurately discriminate the type of resin contained in the sample.

The type of resin thus obtained is output from the output section 14 (corresponding to "discrimination result display section" of the invention) as display or printing (step S10).

Incidentally, when a plurality of types of resins is contained in the sample 2, the C/R ratio of the sample is the sum of the values obtained by multiplying the mixing ratio of each resin by the C/R ratio of the resin pure substance. Therefore, as a result of determining the difference between the C/R ratio calculated for the sample 2 and the C/R ratio of each resin type in the table, when the difference exceeds a predetermined value for any of the resin types, or when the difference deviates from a predetermined numerical range centered on the value of the C/R ratio for any of the resin types, the discrimination section 13 may determine that a plurality of types of resins is included, thereby discriminating the type of resin contained in the sample by a method to be described below.

First, the discrimination section 13 arranges the C/R ratio in the table of Table 1 in the order in which a difference from the C/R ratio calculated for the sample is small, and the following relational expression (1) is set with the value of the C/R ratio as an independent variable ($X1$, $X2$, and $X3$, ...) and the C/R ratio calculated for the sample as the dependent variable $Y$.

$$Y = a \cdot X1 + b \cdot X2 + c \cdot X3 + \ldots \quad (1)$$

Here, $a$, $b$, $c$ ... indicates coefficients representing mixing ratio ($a+b+c+ \ldots =1$) of each resin. The discrimination section 13 determines the value of each coefficient by regression analysis, while changing the values of the coefficients $a$, $b$, $c$, and the like. For such regression analysis, well-known analysis software such as "Excel" can be used.

Further, the type of resin contained in the sample 2 is discriminated on the basis of the value of the obtained coefficient as a result of the regression analysis. For example, in order from the largest coefficient value, the resin type corresponding to the third highest C/R ratio is estimated as a combination of types of resins included in the sample 2. Further, the resin type corresponding to the C/R ratio at which the value of the coefficient is equal to or greater than the predetermined set minimum value may be estimated as the combination of the types of resins included in the sample 2.

Furthermore, when a plurality of relational expressions (solutions) is obtained as a result of the regression analysis, a combination of types of resins contained in the sample is estimated for all of these relational expressions, and these may be used as candidates for combination of resin types. Further, a combination of candidate resin types is displayed by a display screen or printing, and an analyzer may select an appropriate combination from among them. Further, for all of the plurality of relational expressions, the degree of coincidence between the value of Y obtained from each relational expression and Y (C/R ratio) calculated for the sample is calculated, and the degree of coincidence may be displayed together with a combination of the resin type as a candidate by the display screen or printing. In this case, the display unit or the printing unit for displaying the display screen corresponds to the coincidence degree display section of the invention.

According to such a configuration, even when a plurality of types of resins is contained in the sample, the type of these resins can be discriminated. In addition, if the degree of coincidence is displayed together with the combination of the resin type as a candidate, the analyzer can select the combination of the resin types with reference to the degree of coincidence.

In the above embodiment, the process of determining the type of resin in the sample 2 from the table stored in the storage section 131 and the process of determining the type of resin in the sample 2 by regression analysis are used together. However, only one process may be used for the determination process of the type of resin in the sample 2.

Further, the invention is not limited to the above-described embodiments. As long as it is possible to create a spectrum from a detection signal of X-rays emitted from a sample and to obtain a ratio of Compton scattering intensity and Rayleigh scattering intensity from the spectrum, any type of X-ray analyzer may be used, and the target material and the X-ray detector are not limited to those described in the examples.

The invention claimed is:

1. A resin discriminating apparatus comprising:
    a) an X-ray source which emits X-rays;
    b) an X-ray detector which detects X-rays emitted from a sample irradiated with X-rays;
    c) a spectrum creating unit which creates a spectrum on the basis of a detection signal obtained by the X-ray detector;
    d) a scattering intensity ratio calculation unit which detects a spectral line due to Compton scattering and a spectral line due to Rayleigh scattering derived from a target element of the X-ray source on the spectrum, and calculates a scattering intensity ratio which is a ratio of the Rayleigh scattering intensity and the Compton scattering intensity;
    e) a resin type discrimination unit which discriminates the type of resin contained in the sample from the scattering intensity ratio, and
    f) a storage section which stores a scattering intensity ratio previously obtained for a plurality of known resins,
    wherein the resin type discrimination unit discriminates the type of resin contained in the sample, by comparing the scattering intensity ratio calculated by the scattering intensity ratio calculation unit with the plurality of scattering intensity ratios stored in the storage section,
    wherein the resin type discrimination unit obtains a relational expression in which a plurality of scattering intensity ratios stored in the storage section is set as independent variables and a scattering intensity ratio calculated by the scattering intensity ratio calculation unit is set as a dependent variable by regression analysis, and discriminates the type and a mixing ratio of the resin contained in the sample from coefficients of the respective independent variables in the obtained relational expression,
    wherein, when a plurality of the relational expressions is obtained by the regression analysis, the resin type discrimination unit discriminates the type of resin contained in the sample from the coefficients of the respective independent variables in each relational expression, and obtains a degree of coincidence between the scattering intensity ratio obtained from the relational expression and the scattering intensity ratio calculated by the scattering intensity ratio calculation unit, and
    wherein the resin discriminating apparatus further comprises a coincidence degree display section which displays the type of resin contained in the sample discriminated by the resin discrimination unit for each of the plurality of relational expressions and the degree of coincidence.

2. The resin discriminating apparatus according to claim 1, further comprising:
    a discrimination result display section which displays a result discriminated by the resin type discrimination unit.

3. The resin discriminating apparatus according to claim 1, wherein the resin type discrimination unit detects fluorescent X-rays emitted from the sample on the spectrum, and discriminates the type of resin contained in the sample from the intensity of the fluorescent X-ray and the scattering intensity ratio calculated by the scattering intensity ratio calculation unit.

4. A resin discriminating method comprising:
    irradiating a sample with X-rays emitted from an X-ray source;
    analyzing X-rays emitted from the sample accordingly;
    calculating a scattering intensity ratio which is a ratio of a Compton scattering intensity to a Rayleigh scattering intensity derived from a target element of the X-ray source; and
    discriminating the type of resin contained in the sample from the scattering intensity ratio,
    wherein a relational expression in which a scattering intensity ratio determined in advance for a plurality of known resins is set as an independent variable and a scattering intensity ratio calculated for the sample is set as a dependent variable is obtained by regression analysis, and a type and a mixing ratio of the resin contained in the sample is discriminated from coefficients of each independent variable in the obtained relational expression,
    wherein, when a plurality of the relational expressions is obtained by the regression analysis, the type of resin contained in the sample is discriminated from the coefficients of the respective independent variables in each relational expression, and a degree of coincidence between the scattering intensity ratio from the relational expression and the scattering intensity ratio calculated from the sample is obtained, and
    wherein the method further includes displaying the type of resin contained in the sample discriminated for each of the plurality of relational expressions and the degree of coincidence.

5. The resin discriminating method according to claim 4, wherein the type of resin contained in the sample is discriminated by comparing the scattering intensity ratio calculated for the sample with a scattering intensity ratio obtained in advance for a plurality of known resins.

6. The resin discriminating method according to claim 4, wherein X-rays emitted from the sample are analyzed in accordance with irradiation of X-rays on the sample to calculate the intensity of fluorescent X-rays emitted from the sample, and the type of the resin contained in the sample is discriminated from the intensity of the fluorescent X-rays and the scattering intensity ratio calculated for the sample.

* * * * *